(12) United States Patent
Takasu et al.

(10) Patent No.: US 8,809,567 B2
(45) Date of Patent: Aug. 19, 2014

(54) METHOD FOR PRODUCING SILYLENOL ETHERS

(75) Inventors: Kiyosei Takasu, Kyoto (JP); Yoshiji Takemoto, Kyoto (JP); Kei Kurahashi, Kyoto (JP)

(73) Assignee: Kyoto University, Kyoto (JP)

( * ) Notice: Subject to any disclaimer, the term of this patent is extended or adjusted under 35 U.S.C. 154(b) by 8 days.

(21) Appl. No.: 13/582,577

(22) PCT Filed: Mar. 3, 2011

(86) PCT No.: PCT/JP2011/054945
§ 371 (c)(1),
(2), (4) Date: Nov. 12, 2012

(87) PCT Pub. No.: WO2011/108661
PCT Pub. Date: Sep. 9, 2011

(65) Prior Publication Data
US 2013/0053567 A1    Feb. 28, 2013

(30) Foreign Application Priority Data
Mar. 4, 2010 (JP) ................. 2010-048290

(51) Int. Cl.
*C07F 7/04* (2006.01)
(52) U.S. Cl.
USPC ........................................ 556/470
(58) Field of Classification Search
USPC ........................................ 556/470
See application file for complete search history.

(56) References Cited

FOREIGN PATENT DOCUMENTS

| JP | 11-116582 A | 4/1999 |
|----|-------------|--------|
| JP | 11-217391 A | 8/1999 |

OTHER PUBLICATIONS

Dorwald F. A. Side Reactions in Organic Synthesis, 2005, Wiley: VCH, Weinheim p. IX of Preface p. 1-15.*
Olah et al. (Journal of Organic Chemistry 1981, 46(25), 5212-5215.*
Mathieu et al., *Tetrahedron*, 58 (41): 8219-8226 (2002).
Mathieu et al., *Tetrahedron Letters*, 38 (31): 5497-5500 (1997).
Olah et al., *J. Org. Chem.*, 46 (25): 5212-5214 (1981).
Tanabe et al., *Chemical Communications*: 1628-1629 (2002).
Japanese Patent Office, International Search Report in International Patent Application No. PCT/JP2011/054945 (May 17, 2011).
International Bureau of WIPO, International Preliminary Report on Patentability in International Patent Application No. PCT/JP2011/054945 (Oct. 2, 2012).
Kuhnert et al., Tetrahedron Letters, 39(20): 3215-3216 (1998).
European Patent Office, Extended European Search Report in European Patent Application No. 11750770.7 (Apr. 24, 2014).

* cited by examiner

*Primary Examiner* — Nizal Chandrakumar
(74) *Attorney, Agent, or Firm* — Leydig, Voit & Mayer, Ltd.

(57) ABSTRACT

The invention relates to a method for producing silyl enol ether compound (3) by reacting ketone or aldehyde compound (1) with allylsilane compound (2) in the presence of a base and 0.00001 to 0.5 equivalents of an acid catalyst relative to ketone or aldehyde compound (1).

$$R^5-\underset{\underset{R^6}{|}}{\overset{\overset{R^4}{|}}{Si}}-\underset{\underset{R^{11}}{|}}{\overset{\overset{R^{10}}{|}}{C}}-\overset{\overset{R^7}{|}}{C}=CR^8R^9$$

$$R^1-\overset{\overset{O}{\|}}{C}-CHR^2R^3 \quad \xrightarrow{(2)}$$
(1)

$$R^5-\underset{\underset{R^6}{|}}{\overset{\overset{R^4}{|}}{Si}}-O-\overset{}{C}=CR^2R^3$$
$$\phantom{R^5-Si-O-}\overset{}{R^1}$$
(3)

6 Claims, No Drawings

METHOD FOR PRODUCING SILYLENOL ETHERS

CROSS-REFERENCE TO RELATED APPLICATIONS

This patent application is the U.S. national phase of International Patent Application PCT/JP2011/054945, filed on Mar. 3, 2011, which claims the benefit of Japanese Patent Application No. 2010-048290, filed on Mar. 4, 2010, which are incorporated by reference in their entireties herein.

TECHNICAL FIELD

The present invention relates to a method for producing silyl enol ethers useful as organic synthetic intermediates, which method is convenient, has broad utility and places a low environmental load.

BACKGROUND ART

Silyl enol ethers are important synthetic intermediates for organic synthesis, and can be used as a synthetic intermediate for pharmaceutical products and organic materials, or a treatment agent in various fields of surface treatment.

Representative general production methods of a silyl enol ether using ketone (or aldehyde) as a starting material are three methods shown below.

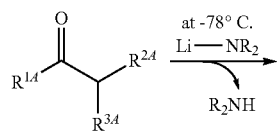

(A)

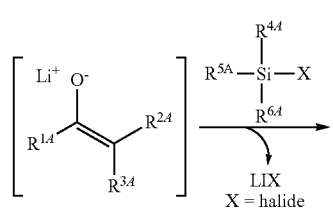

(B)

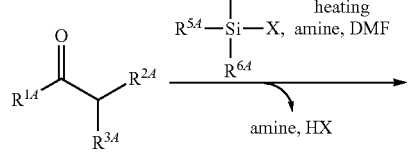

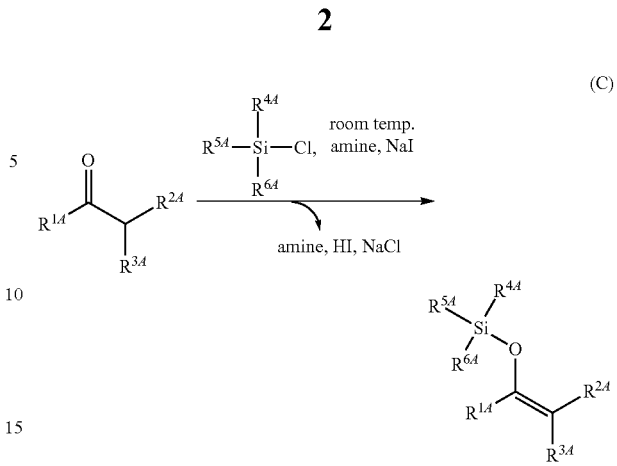

(C)

Method (A) is a method most generally used, which requires a stoichiometric amount of reactants and, as a result, produces a stoichiometric amount of amine and lithium halide as a waste. Generally, moreover, low temperature conditions are required during preparation of lithium enolate. Method (B) is considered to be a comparatively convenient method; however, it is difficult to apply except for the synthesis of trimethylsilyl enol ether ($R^{4A}$-$R^{6A}$=Me). In this case, again, a stoichiometric amount of an amine/hydrogen halide salt is produced as a waste. As a reaction temperature, a high temperature of not less than 100° C. is often required. Method (C) is also a comparatively convenient method, and the reaction temperature is around room temperature. In this case, again, produced as a waste is a stoichiometric amount of an amine/hydrogen halide salt and sodium chloride. Depending on the substrate, the reaction may not proceed sufficiently.

Methods (1) to (4) shown below have been further reported the production methods of a silyl enol ether.

(1) Chemical Communications, 2002, pp. 1628-1629 (non-patent document 1)

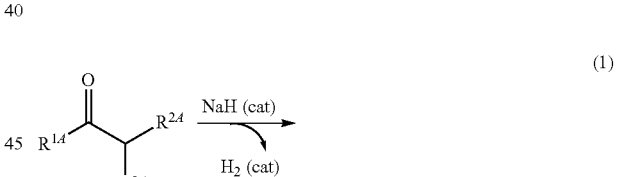

(1)

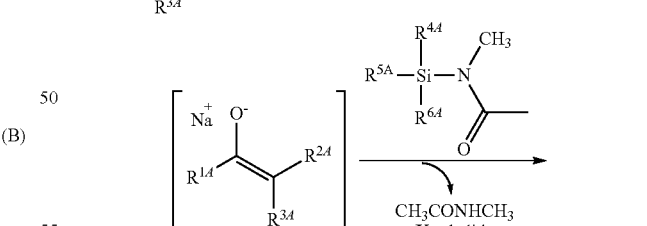

(2) JP-A-11-217391 (patent document 1)

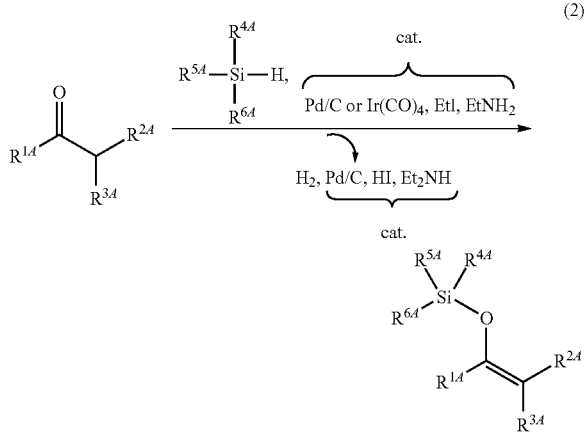

(3) Journal of Organic Chemistry, 1981, Vol. 46, pp. 5212-5214 (non-patent document 2)

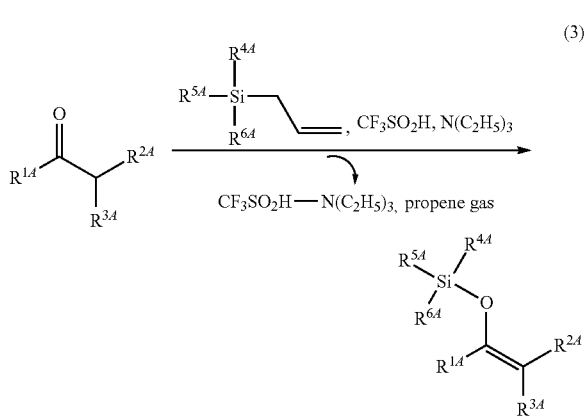

(4) JP-A-11-116582 (patent document 2)

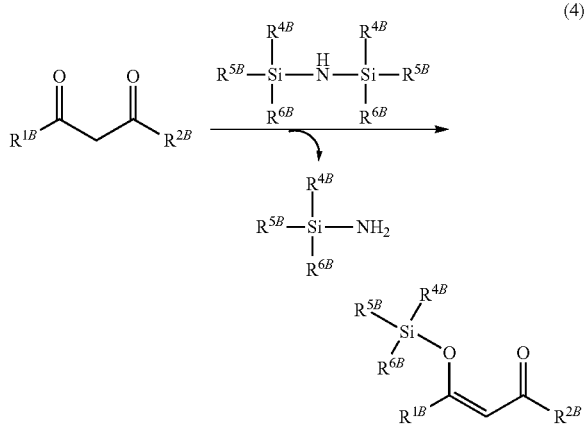

Method (1) is a synthesis method using a stoichiometric amount of N-methyl-N-(trimethylsilyl)acetamide as a silylating agent in the presence of a catalytic amount of a base. As a waste, a stoichiometric amount of N-methylacetamide and a trace amount of a hydrogen gas are produced. However, it has a problem in that preparation of a silylating agent (N-methyl-N-(trimethylsilyl)acetamide) used here results in the production of a stoichiometric amount of a salt of a base and hydrogen halide as a waste. In addition, handling of the silylating agent is not easy.

Method (2) is a method using a catalytic amount of groups 7 to 10 transition metal catalysts, ethyl iodide and ethylamine, and a stoichiometric amount of silane (silyl hydride). The waste in this method is considered to be less as compared to the above-mentioned methods (A) to (C). However, it discharges a trace amount of a transition metal and an amine/hydrogen halide salt which place high environmental load. In addition, the co-presence of a transition metal and a hydrogen gas may be dangerous since it sometimes causes explosion.

Method (3) is a method using 1.5 equivalents of allylsilane, 1.5 equivalents of trifluoromethanesulfonic acid and 2 equivalents of triethylamine as reactants relative to ketone as a starting material. In this case, ketone as a starting material and triethylamine need to be added after preparation of a chemically active species by blending allylsilane and trifluoromethanesulfonic acid, and the operation process is complicated. In addition, a high number of waste materials are produced in a stoichiometric amount.

Method (4) has a problem in that the starting material is limited to a 1,3-dicarbonyl compound alone besides production of a stoichiometric amount of amine.

Taking all these aspects into consideration, when an organic compound is produced in a large amount, a reaction producing the least possible waste (coproduct) is desirable. In addition, there is a problem in that hydrogen halide generated not only corrodes reactors and incineration system, but also places a high environmental load. Therefore, the development of a method to solve the problem has been desired.

DOCUMENT LIST

Patent Documents patent document 1: JP-A-11-217391
patent document 2: JP-A-11-116582

Non-Patent Documents non-patent document 1: Chemical Communications, 2002, pp. 1628-1629
non-patent document 2: Journal of Organic Chemistry, 1981, Vol. 46, pp. 5212-5214

SUMMARY OF THE INVENTION

Problems to be Solved by the Invention

The present invention aims to provide a method for producing a silyl enol ether compound, which is convenient, has highly broad utility and places a low environmental load (less waste).

Means of Solving the Problems

The present inventors have conducted intensive studies in an attempt to solve the aforementioned problems and found that a method for producing a silyl enol ether compound, which places a low environmental load (extremely small waste), is convenient, and has highly broad utility can be provided by reacting a ketone or aldehyde compound with an allylsilane compound in the presence of a base and a catalytic amount of an acid catalyst, which resulted in the completion of the present invention.

Accordingly, the present invention provides the following.

[1] A method for producing a silyl enol ether compound represented by the formula (3)

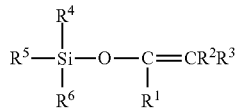

(3)

wherein $R^1$ is a hydrogen atom, an alkoxy group optionally having substituent(s), an aryloxy group optionally having substituent(s), a dialkylamino group optionally having substituent(s), a diarylamino group optionally having substituent(s), an N-alkyl-N-arylamino group optionally having substituent(s), an alkylthio group optionally having substituent(s), an arylthio group optionally having substituent(s), an alkyl group optionally having substituent(s), a cycloalkyl group optionally having substituent(s), an aralkyl group optionally having substituent(s), an alkenyl group optionally having substituent(s), an alkynyl group optionally having substituent(s), an aryl group optionally having substituent(s) or a heteroaryl group optionally having substituent(s);

$R^2$ and $R^3$ are each independently a hydrogen atom, a halogen atom, an alkyl group optionally having substituent(s), a cycloalkyl group optionally having substituent(s), an aralkyl group optionally having substituent(s), an aryl group optionally having substituent(s) or a heteroaryl group optionally having substituent(s);

$R^1$ and $R^3$, $R^1$ and $R^2$, or $R^2$ and $R^3$ optionally form, together with the carbon atom(s) bonded thereto, a ring optionally having substituent(s);

$R^4$, $R^5$ and $R^6$ are each independently a hydrogen atom, a halogen atom, an alkoxy group optionally having substituent(s), an aryloxy group optionally having substituent(s), an alkyl group optionally having substituent(s), an alkenyl group optionally having substituent(s), an alkynyl group optionally having substituent(s), a cycloalkyl group optionally having substituent(s), a cycloalkenyl group optionally having substituent(s), an aralkyl group optionally having substituent(s), an aryl group optionally having substituent(s), a heteroaryl group optionally having substituent(s) or a silyl group optionally having substituent(s); and two of $R^4$, $R^5$ and $R^6$ optionally form a ring together with the silicon atom bonded thereto, which comprises reacting a ketone or aldehyde compound represented by the formula (1)

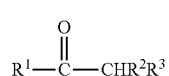

(1)

wherein each symbol is as defined above, with an allylsilane compound represented by the formula (2)

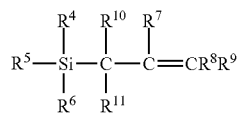

(2)

wherein $R^7$, $R^8$, $R^9$, $R^{10}$ and $R^{11}$ are each independently a hydrogen atom, an alkyl group optionally having substituent(s), an alkenyl group optionally having substituent(s), an alkynyl group optionally having substituent(s), a cycloalkyl group optionally having substituent(s), a cycloalkenyl group optionally having substituent(s), an aralkyl group optionally having substituent(s), an aryl group optionally having substituent(s), a heteroaryl group optionally having substituent(s), a halogen atom, a hydroxyl group, an alkoxy group, an amino group or a silyl group optionally having substituent(s);

two of $R^7$, $R^8$, $R^9$, $R^{10}$ and $R^{11}$ optionally form, together with the carbon atom(s) bonded thereto, a ring optionally having substituent(s); and other symbols are as defined above, in the presence of a base and 0.00001 to 0.5 equivalents of an acid catalyst relative to a ketone or aldehyde compound represented by the formula (1).

[2] A method for producing a 1-siloxydiene compound represented by the formula (16)

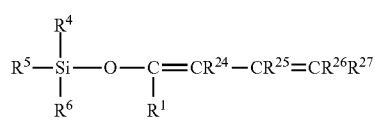

(16)

wherein $R^1$ is a hydrogen atom, an alkoxy group optionally having substituent(s), an aryloxy group optionally having substituent(s), a dialkylamino group optionally having substituent(s), a diarylamino group optionally having substituent(s), an N-alkyl-N-arylamino group optionally having substituent(s), an alkylthio group optionally having substituent(s), an arylthio group optionally having substituent(s), an alkyl group optionally having substituent(s), a cycloalkyl group optionally having substituent(s), an aralkyl group optionally having substituent(s), an alkenyl group optionally having substituent(s), an alkynyl group optionally having substituent(s), an aryl group optionally having substituent(s) or a heteroaryl group optionally having substituent(s);

$R^4$, $R^5$ and $R^6$ are each independently a hydrogen atom, a halogen atom, an alkoxy group optionally having substituent(s), an aryloxy group optionally having substituent(s), an alkyl group optionally having substituent(s), an alkenyl group optionally having substituent(s), an alkynyl group optionally having substituent(s), a cycloalkyl group optionally having substituent(s), a cycloalkenyl group optionally having substituent(s), an aralkyl group optionally having substituent(s), an aryl group optionally having substituent(s), a heteroaryl group optionally having substituent(s) or a silyl group optionally having substituent(s);

two of $R^4$, $R^5$ and $R^6$ optionally form a ring together with the silicon atom bonded thereto;

$R^{24}$, $R^{25}$, $R^{26}$ and $R^{27}$ are each independently a hydrogen atom, a halogen atom, an alkyl group optionally having substituent(s), a cycloalkyl group optionally having substituent(s), an aralkyl group optionally having substituent(s), an aryl group optionally having substituent(s) or a heteroaryl group optionally having substituent(s); and $R^1$ and $R^{25}$, $R^{25}$ and $R^{26}$, $R^{25}$ and $R^{27}$, or $R^{26}$ and $R^{27}$ optionally form, together with the carbon atom(s) bonded thereto, a ring optionally having substituent(s); or $R^1$ and $R^{25}$ are optionally bonded, and $R^{25}$ and $R^{26}$ are optionally bonded, to form, together with the carbon atoms bonded thereto, a fused ring optionally having substituent(s), which comprises reacting an α,β-unsaturated ketone or aldehyde compound represented by the formula (15)

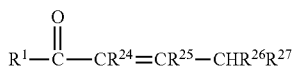

(15)

wherein each symbol is as defined above, with an allylsilane compound represented by the formula (2)

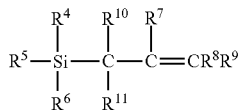

(2)

wherein $R^7$, $R^8$, $R^9$, $R^{10}$ and $R^{11}$ are each independently a hydrogen atom, an alkyl group optionally having substituent(s), an alkenyl group optionally having substituent(s), an alkynyl group optionally having substituent(s), a cycloalkyl group optionally having substituent(s), a cycloalkenyl group optionally having substituent(s), an aralkyl group optionally having substituent(s), an aryl group optionally having substituent(s), a heteroaryl group optionally having substituent(s), a halogen atom, a hydroxyl group, an alkoxy group, an amino group or a silyl group optionally having substituent(s);

two of $R^7$, $R^8$, $R^9$, $R^{10}$ and $R^{11}$ optionally form, together with the carbon atom(s) bonded thereto, a ring optionally having substituent(s); and other symbols are as defined above, in the presence of a base and 0.00001 to 0.5 equivalents of an acid catalyst relative to the α,β-unsaturated ketone or aldehyde compound represented by the formula (15).

[3] The method of the aforementioned [1] or [2], wherein the acid catalyst is at least one selected from a sulfonyl compound represented by the formula (4) or (5)

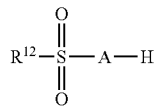

(4)

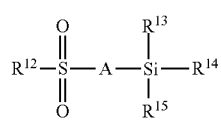

(5)

wherein A is a nitrogen atom, an oxygen atom, a carbon atom, a sulfur atom or a phosphorus atom, which is unsubstituted or has one or more substituents as chemically allowed;

$R^{12}$ is a halogen atom, an alkyl group optionally substituted by halogen atom(s), an aryl group optionally substituted by halogen atom(s) or a heterocyclic group optionally substituted by halogen atom(s);

$R^{13}$, $R^{14}$ and $R^{15}$ are each independently a hydrogen atom, an alkyl group optionally having substituent(s), an alkenyl group optionally having substituent(s), an alkynyl group optionally having substituent(s), a cycloalkyl group optionally having substituent(s), a cycloalkenyl group optionally having substituent(s), an aralkyl group optionally having substituent(s), an aryl group optionally having substituent(s), a heteroaryl group optionally having substituent(s), a halogen atom, a hydroxyl group, an alkoxy group, an amino group or a silyl group optionally having substituent(s); and two of $R^{13}$, $R^{14}$ and $R^{15}$ optionally form a ring together with the silicon atom bonded thereto.

[4] The method of the aforementioned [3], wherein the acid catalyst shows pKa of 8 or below in acetic acid.

[5] The method of the aforementioned [1] or [2], wherein the acid catalyst is at least one selected from a sulfonyl compound represented by the formula (6), (7), (8), (9) or (10)

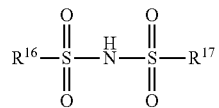

(6)

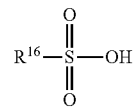

(7)

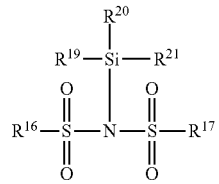

(8)

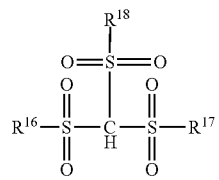

(9)

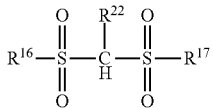

(10)

wherein $R^{16}$, $R^{17}$ and $R^{18}$ are each independently a halogen atom, an alkyl group optionally substituted by halogen atom(s), an aryl group optionally substituted by halogen atom(s) or a heterocyclic group optionally substituted by halogen atom(s); and $R^{19}$, $R^{20}$, $R^{21}$ and $R^{22}$ are each independently a hydrogen atom, an alkyl group optionally having substituent(s), an alkenyl group optionally having substituent(s), an alkynyl group optionally having substituent(s), a cycloalkyl group optionally having substituent(s), a cycloalkenyl group optionally having substituent(s), an aralkyl group optionally having substituent(s), an aryl group optionally having substituent(s), a heteroaryl group optionally having substituent(s), a halogen atom, a hydroxyl group, an alkoxy group, an amino group or a silyl group optionally having substituent(s).

[6] The method of the aforementioned [1] or [2], wherein the acid catalyst is a sulfonyl compound represented by the formula (6)

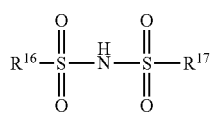
(6)

wherein $R^{16}$ and $R^{17}$ are each independently a halogen atom, an alkyl group optionally substituted by halogen atom(s), an aryl group optionally substituted by halogen atom(s) or a heterocyclic group optionally substituted by halogen atom(s).

[7] The method of the aforementioned [1] or [2], wherein the acid catalyst is at least one selected from a sulfonyl compound represented by the formula (11), (12) or (13)

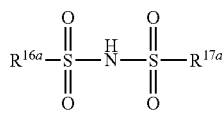
(11)

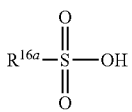
(12)

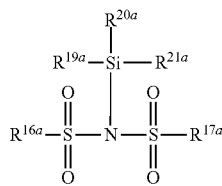
(13)

wherein $R^{16a}$ and $R^{17a}$ are each independently an alkyl group substituted by two or more fluorine atoms, or an aryl group substituted by two or more fluorine atoms; and
$R^{19a}$, $R^{20a}$ and $R^{21a}$ are each independently an alkyl group.

[8] The method of the aforementioned [1] or [2], wherein the acid catalyst is a sulfonyl compound represented by the formula (11)

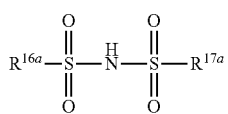
(11)

wherein $R^{16a}$ and $R^{17a}$ are each independently an alkyl group substituted by two or more fluorine atoms, or an aryl group substituted by two or more fluorine atoms.

[9] The method of any of the aforementioned [1] to [8], wherein the amount of the acid catalyst to be used is 0.001 to 0.5 equivalents relative to the ketone or aldehyde compound represented by the formula (1) or the α,β-unsaturated ketone or aldehyde compound represented by the formula (15).

[10] The method of any of the aforementioned [1] to [9], wherein the amount of the base to be used is 0.00001 to 0.5 equivalents relative to the ketone or aldehyde compound represented by the formula (1) or the α,β-unsaturated ketone or aldehyde compound represented by the formula (15).

[11] The method of any of the aforementioned [1] to [9], wherein the amount of the base to be used is 0.001 to 0.5 equivalents relative to the ketone or aldehyde compound represented by the formula (1) or the α,β-unsaturated ketone or aldehyde compound represented by the formula (15).

[12] The method of any of the aforementioned [1] to [11], wherein the allylsilane compound represented by the formula (2) is a compound represented by the formula (14)

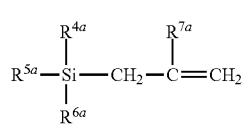
(14)

wherein $R^{4a}$, $R^{5a}$ and $R^{6a}$ are each independently an alkyl group, and $R^{7a}$ is a hydrogen atom, an alkyl group, an aryl group or an aralkyl group.

[13] The method of any of the aforementioned [1] to [12], wherein the reaction is performed using a microreactor.

Effect of the Invention

According to the method of the present invention, a waste (coproduct) generated during a reaction can be extremely less by performing the reaction by using an allylsilane compound as a silylating agent, and in the presence of a base and a catalytic amount of an acid catalyst. As a result, it affords an advantage that the purification method of the object product after the reaction is convenient. It also affords an advantage that hydrogen halide or a salt thereof is not produced as a reaction waste.

Since the reaction mixture after completion of the reaction contains almost only the object product and unreacted starting materials, purification is extremely easy. For example, the object product can be purified by concentration only or distillation of the reaction mixture. Particularly, when an allylsilane compound of the formula (2) wherein $R^7$, $R^8$, $R^9$, $R^{10}$ and $R^{11}$ are each a hydrogen atom is used as a silylating agent, the resulting wastes are gaseous propene gas ($CH_3$—$CH$=$CH_2$) and a catalytic amount of a salt of the acid catalyst and the base. When an allylsilane compound of the formula (2) wherein $R^7$ is a methyl group, and $R^8$, $R^9$, $R^{10}$ and $R^{11}$ are each a hydrogen atom is used, the resulting wastes are isobutene gas (($CH_3$)$_2$$C$=$CH_2$) and a catalytic amount of a salt of the acid catalyst and the base. Since propene gas and isobutene gas are released from the reaction mixture, it affords an advantage that the purification method of the object product is convenient. A salt of the acid catalyst and the base can be recovered and reused.

When an allylsilane compound of the formula (2) wherein $R^7$ is a methyl group or phenyl group, and $R^8$, $R^9$, $R^{10}$ and $R^{11}$ are each a hydrogen atom is used, it affords an advantage that the reaction proceeds under mild conditions around room temperature (about 1° C. to about 30° C.)

Moreover, as a reaction operation, since it uses reagents and a silylating agent (allylsilane compound), which are safe and easy to handle, and does not require control of the reaction temperature to a very low temperature, it is a convenient method as compared to conventional methods.

Hence, according to the present invention, a method for producing a silyl enol ether compound, which is convenient, has highly broad utility, and places a low environmental load (extremely small waste), can be provided.

DESCRIPTION OF EMBODIMENTS

The present invention is explained in detail below.

The "alkyl group" may be straight chain or branched chain and, for example, $C_{1-12}$ alkyl group (e.g., methyl, ethyl, propyl, isopropyl, butyl, isobutyl, sec-butyl, tert-butyl, pentyl, isopentyl, tert-pentyl, hexyl, heptyl, octyl, nonyl, decyl, undecyl, dodecyl etc.) can be mentioned, with preference given to $C_{1-8}$ alkyl group (e.g., methyl, ethyl, propyl, isopropyl, butyl, isobutyl, sec-butyl, tert-butyl etc.).

The "alkenyl group" may be straight chain or branched chain and, for example, $C_{2-12}$ alkenyl group (e.g., vinyl, allyl, isopropenyl, 1-butenyl, 2-butenyl, 3-butenyl, 2-methyl-2-propenyl, 1-methyl-2-propenyl, 2-methyl-1-propenyl etc.) can be mentioned, with preference given to $C_{2-8}$ alkenyl group.

The "alkynyl group" may be straight chain or branched chain and, for example, $C_{2-12}$ alkynyl group (e.g., ethynyl, propargyl, 1-butynyl, 2-butynyl, 3-butynyl, 1-hexynyl etc.) can be mentioned, with preference given to $C_{2-8}$ alkynyl group.

Examples of the "cycloalkyl group" include $C_{3-12}$ cycloalkyl group (e.g., cyclopropyl, cyclobutyl, cyclopentyl, cyclohexyl, cycloheptyl, cyclooctyl etc.), with preference given to $C_{3-8}$ cycloalkyl group.

Examples of the "cycloalkenyl group" include $C_{3-12}$ cycloalkenyl group (e.g., 2-cyclopenten-1-yl, 1-cyclohexen-1-yl, 1,3-cyclohexadienyl etc.), with preference given to $C_{3-8}$ cycloalkenyl group.

Examples of the "aryl group" include $C_{6-14}$ aryl group (e.g., phenyl, 1-naphthyl, 2-naphthyl, 2-biphenylyl, 3-biphenylyl, 4-biphenylyl, 2-anthryl etc.), with preference is given to $C_{6-10}$ aryl group, more preferably, phenyl group.

Examples of the "aralkyl group" include mono, di or tri ($C_{6-14}$ aryl)-$C_{1-8}$ alkyl group (e.g., benzyl, 1-phenethyl, 2-phenethyl, 1-phenylpropyl, 2-phenylpropyl, 3-phenylpropyl, 1-naphthylmethyl, 2-naphthylmethyl, benzhydryl, trityl etc.), with preference given to $C_{6-14}$ aryl-$C_{1-8}$ alkyl group, more preferably phenyl-$C_{1-8}$ alkyl group.

As the "heteroaryl group", a monovalent group obtained by removing any one hydrogen atom from 5- to 14-membered (preferably 5- to 10-membered, particularly preferably 5- or 6-membered) aromatic heterocycle (which may include monocyclic, bicyclic, tricyclic or tetracyclic ones) containing, besides carbon atom, 1 to 4 hetero atoms selected from a nitrogen atom, a sulfur atom and an oxygen atom, and the like can be mentioned. Examples of the above-mentioned "5- to 14-membered (preferably 5- to 10-membered) aromatic heterocycle" include aromatic heterocycles such as thiophene, benzo[b]thiophene, furan, benzo[b]furan, benzimidazole, oxazole, benzoxazole, isoxazole, benzisoxazole, thiazole, benzothiazole, isothiazole, benzisothiazole, oxadiazole, thiadiazole, naphtho[2,3-b]thiophene, naphtho[2,3-b]furan, pyrrole, imidazole, pyrazole, triazole, tetrazole, pyridine, pyrazine, pyrimidine, pyridazine, triazine, furazan, indole, isoindole, indazole, purine, pteridine, isoquinoline, quinoline, phthalazine, naphthyridine, quinoxaline, quinazoline, cinnoline, carbazole, β-carboline, phenanthridine, acridine, phenazine, phenothiazine, phenoxazine and the like, or a ring formed by condensation of these rings (preferably monocycle) with one or more (preferably 1 or 2) aromatic rings (e.g., benzene ring etc.), or a ring formed by condensation of heterocycles selected from these heterocycles and the like.

Preferred as the "heteroaryl group" is a 5- to 14-membered (preferably 5- to 10-membered) (monocyclic or bicyclic) heteroaryl group containing, besides carbon atom, preferably 1 to 4 hetero atoms of one or two kinds selected from a nitrogen atom, a sulfur atom and an oxygen atom. Specifically, for example, heteroaryl groups such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 5-pyrimidinyl, 3-pyrrolyl, 2-imidazolyl, 4-imidazolyl, 3-pyridazinyl, 2-thiazolyl, 4-thiazolyl, 3-isothiazolyl, 2-oxazolyl, 4-oxazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like can be mentioned.

Examples of the "halogen atom" include a fluorine atom, a chlorine atom, a bromine atom, and an iodine atom.

The "alkoxy group" may be straight chain or branched chain and, for example, $C_{1-12}$ alkoxy group (e.g., methoxy, ethoxy, propoxy, isopropoxy, butoxy, isobutoxy, sec-butoxy, tert-butoxy, pentyloxy, isopentyloxy, tert-pentyloxy, hexyloxy, heptyloxy, octyloxy, nonyloxy, decyloxy, undecyloxy, dodecyloxy etc.) can be mentioned, with preference given to $C_{1-8}$ alkoxy group (e.g., methoxy, ethoxy, propoxy, isopropoxy, butoxy, isobutoxy, sec-butoxy, tert-butoxy etc.).

Examples of the "aryloxy group" include $C_{6-14}$ aryloxy group (e.g., phenoxy, 1-naphthyloxy, 2-naphthyloxy, 2-biphenylyloxy, 3-biphenylyloxy, 4-biphenylyloxy, 2-anthryloxy etc.), with preference given to a $C_{6-10}$ aryloxy group, more preferably a phenoxy group.

Examples of the "dialkylamino group" include a dialkylamino group wherein the alkyl moiety is the same or different "alkyl group" as defined above, such as di($C_{1-12}$ alkyl) amino group (e.g., N,N-dimethylamino, N,N-diethylamino, N,N-dipropylamino, N,N-diisopropylamino, N,N-dibutylamino, N,N-diisobutylamino, N,N-di-sec-butylamino, N,N-di-tert-butylamino, N,N-dipentylamino, N,N-diisopentylamino, N,N-dineopentylamino, N,N-dihexylamino, N,N-diheptylamino, N-ethyl-N-methylamino, N-methyl-N-propylamino, N-isopropyl-N-methylamino, N-butyl-N-methylamino, N-isobutyl-N-methylamino, N-sec-butyl-N-methylamino, N-tert-butyl-N-methylamino, N-methyl-N-pentylamino, N-isopentyl-N-methylamino, N-methyl-N-neopentylamino, N-hexyl-N-methylamino, N-heptyl-N-methylamino, N-methyl-N-octylamino, N-methyl-N-nonylamino, N-decyl-N-methylamino, N-methyl-N-undecylamino, N-dodecyl-N-methylamino etc.), with preference given to di($C_{1-8}$ alkyl)amino group.

Examples of the "diarylamino group" include a diarylamino group wherein the aryl moiety is the same or different "aryl group" as defined above, such as di($C_{6-14}$ aryl)amino group (e.g., N,N-diphenylamino, N,N-di(naphthyl)amino, N-naphthyl-N-phenylamino etc.), with preference given to di($C_{6-10}$ aryl)amino group, more preferably a diphenylamino group.

Examples of the "N-alkyl-N-arylamino group" include an N-alkyl-N-arylamino group wherein the alkyl moiety is the "alkyl group" as defined above and the aryl moiety is the "aryl group" as defined above, such as N—($C_{1-12}$ alkyl)-N—($C_{6-14}$ aryl)amino group (e.g., N-methyl-N-phenylamino, N-ethyl-N-phenylamino, N-phenyl-N-propylamino etc.), with preference given to N—($C_{1-8}$ ($C_{6-10}$ aryl)amino group.

Examples of the "alkylthio group" include an alkylthio group wherein the alkyl moiety is the "alkyl group" as defined above, such as $C_{1-12}$ alkylthio group (e.g., methylthio, ethylthio, propylthio, isopropylthio, butylthio, isobutylthio, sec-butylthio, tert-butylthio, pentylthio, isopentylthio, tert-pentylthio, hexylthio, heptylthio, octylthio, nonylthio, decylthio, undecylthio, dodecylthio etc.), with preference given to $C_{1-8}$ alkylthio group (e.g., methylthio, ethylthio, propylthio, isopropylthio, butylthio, isobutylthio, sec-butylthio, tert-butylthio etc.).

Examples of the "arylthio group" include an arylthio group wherein the aryl moiety is the "aryl group" as defined above, such as $C_{6-14}$ arylthio group (e.g., phenylthio, 1-naphthylthio, 2-naphthylthio, 2-biphenylylthio, 3-biphenylylthio, 4-biphenylylthio, 2-anthrylthio etc.), with preference given to $C_{6-10}$ arylthio group, more preferably a phenylthio group.

The "heterocyclic group" is, for example, a monovalent group obtained by removing any one hydrogen atom from a 5- to 14-membered heterocycle containing, besides carbon atom, 1 to 4 hetero atoms selected from a nitrogen atom, a sulfur atom and an oxygen atom, which may include monocyclic, bicyclic, tricyclic or tetracyclic ones, preferably, (i) a 5- to 14-membered (preferably 5- to 10-membered, particularly preferably 5- or 6-membered) aromatic heterocycle, (ii) a 5- to 10-membered (preferably 5- or 6-membered) non-aromatic heterocycle, or (iii) a 7- to 10-membered bridged heterocycle or the like. Examples of the above-mentioned "5- to 14-membered (preferably 5- to 10-membered) aromatic heterocycle" include aromatic heterocycles such as thiophene, benzo[b]thiophene, furan, benzo[b]furan, benzimidazole, oxazole, benzoxazole, isoxazole, benzisoxazole, thiazole, benzothiazole, isothiazole, benzisothiazole, oxadiazole, thiadiazole, naphtho[2,3-b]thiophene, naphtho[2,3-b]furan, pyrrole, imidazole, pyrazole, triazole, tetrazole, pyridine, pyrazine, pyrimidine, pyridazine, triazine, furazan, indole, isoindole, indazole, purine, pteridine, isoquinoline, quinoline, phthalazine, naphthyridine, quinoxaline, quinazoline, cinnoline, carbazole, β-carboline, phenanthridine, acridine, phenazine, phenothiazine, phenoxazine and the like, or a ring formed by condensation of these rings (preferably monocyclic) and one or more (preferably 1 or 2) aromatic rings (e.g., benzene ring etc.), or a ring formed by condensation of heterocycles selected from these heterocycles and the like. Examples of the above-mentioned "5- to 10-membered non-aromatic heterocycle" include pyrrolidine, imidazolidine, pyrazolidine, pyrazoline, piperidine, piperazine, morpholine, thiomorpholine, oxadiazoline, thiadiazoline, triazoline and the like. Examples of the above-mentioned "7- to 10-membered bridged heterocycle" include quinuclidine, 7-azabicyclo[2.2.1]heptane and the like.

Preferred as the "heterocyclic group" is a 5- to 14-membered (preferably 5- to 10-membered) monocyclic or bicyclic heterocyclic group containing, besides carbon atom, 1 to 4 hetero atoms selected from a nitrogen atom, a sulfur atom and an oxygen atom. Specifically, for example, aromatic heterocyclic groups such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 5-pyrimidinyl, 3-pyrrolyl, 2-imidazolyl, 4-imidazolyl, 3-pyridazinyl, 2-thiazolyl, 4-thiazolyl, 3-isothiazolyl, 2-oxazolyl, 4-oxazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like, non-aromatic heterocyclic groups such as 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like, and the like can be mentioned. Of these, for example, a 5- or 6-membered heterocyclic group containing, besides carbon atom, 1 to 3 hetero atoms selected from a nitrogen atom, a sulfur atom and an oxygen atom and the like are more preferable. Specifically, 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like can be mentioned.

The "substituent" of "an alkyl group optionally having substituents)", "an alkenyl group optionally having substituent(s)", "an alkynyl group optionally having substituent(s)", "a cycloalkyl group optionally having substituent(s)", "a cycloalkenyl group optionally having substituent(s)", "an aryl group optionally having substituent(s)", "an aralkyl group optionally having substituent(s)", "a heteroaryl group optionally having substituent(s)", "a heterocyclic group optionally having substituent(s)", "an alkoxy group optionally having substituent(s)", "an aryloxy group optionally having substituent(s)", "a dialkylamino group optionally having substituent(s)", "a diarylamino group optionally having substituent(s)", "an N-alkyl-N-arylamino group optionally having substituent(s)", "an alkylthio group optionally having substituent(s)", and "an arylthio group optionally having substituent(s)" is not particularly limited as long as it does not influence the reaction and, for example, $C_{1-8}$ alkyl group, $C_{1-8}$ alkoxy group, di($C_{1-8}$ alkyl)amino group, a halogen atom, $C_{6-14}$ aryl-$C_{1-8}$ alkyloxy group (e.g., benzyloxy, 1- or 2-naphthylmethoxy etc.), $C_{2-8}$ alkenyloxy group (e.g., alkyloxy, propargyloxy etc.), nitro group, nitroso group, cyano group, $C_{1-8}$ alkylthio group, $C_{2-8}$ alkenylthio group, tri($C_{1-8}$ alkyl) silyl group (e.g., trimethylsilyl etc.), $C_{1-8}$ alkyloxycarbonyl group (e.g., methoxycarbonyl etc.), $C_{6-14}$ aryloxycarbonyl group (e.g., phenoxycarbonyl etc.), tri($C_{1-8}$ alkyl)silyloxy group (e.g., trimethylsilyloxy etc.), $C_{1-8}$ alkyl-carbonyloxy group (e.g., acetyloxy, propionyloxy etc.), $C_{6-14}$ aryl-carbonyloxy group (e.g., benzoyloxy etc.) and the like can be mentioned. The number of the substituent is not particularly limited, and 1 to 3 is preferable and the substituents may be the same or different.

Examples of "a silyl group optionally having substituent(s)" include silyl group (—$SiH_3$), tri($C_{1-8}$ alkyl) silyl group, tri($C_{6-14}$ aryl) silyl group, di($C_{1-8}$ alkyl) ($C_{6-14}$ aryl) silyl group, ($C_{1-8}$ alkyl)di($C_{6-14}$ aryl) silyl group and the like. Examples of the representative "silyl group optionally having substituent(s)" include trimethylsilyl, triethylsilyl, dimethylethylsilyl, diethylmethylsilyl, tert-butyldimethylsilyl, tert-butyldiethylsilyl, triisopropylsilyl, dimethylisopropylsilyl, diethylisopropylsilyl, tert-butyldimethylsilyl, triphenylsilyl, dimethylphenylsilyl, tert-butyldiphenylsilyl and the like.

Examples of the ring formed by $R^1$ and $R^3$, $R^1$ and $R^2$, $R^1$ and $R^{25}$, $R^{25}$ and $R^{26}$, or $R^{25}$ and $R^{27}$, together with the carbon atoms bonded thereto include (i) a 5- to 12-membered (preferably 5- to 8-membered) hydrocarbon ring optionally having double bond(s) in the ring, (ii) a 5- to 14-membered (preferably 5- to 10-membered) monocyclic or bicyclic heterocycle optionally having double bond(s) in the ring, which contains, besides carbon atom, 1 to 4 hetero atoms selected from a nitrogen atom, a sulfur atom and an oxygen atom, (iii) a steroid nucleus and the like.

Examples of the "steroid nucleus" include a ring represented by the formula

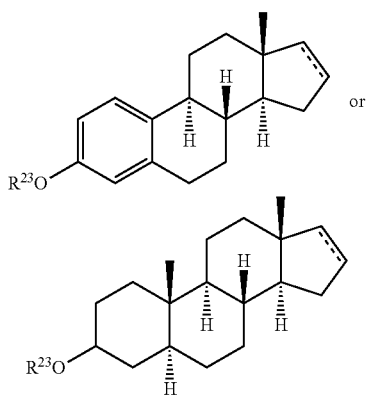

wherein $R^{23}$ is a $C_{1-8}$ alkyl group, and

⸻ is a single bond or a double bond, and the like.

Examples of the ring formed by $R^2$ and $R^3$, or $R^{26}$ and $R^{27}$, together with the carbon atom bonded thereto, include (i) a 3- to 12-membered (preferably 5- to 8-membered) hydrocarbon ring optionally having double bond(s) in the ring (e.g., $C_{3-12}$ cycloalkane, $C_{3-12}$ cycloalkene etc., preferably $C_{5-8}$ cycloalkane, $C_{5-8}$ cycloalkene etc.), (ii) a 3- to 14-membered (preferably 5- to 10-membered) monocyclic or bicyclic heterocycle optionally having double bond(s) in the ring, which contains, besides carbon atom, 1 to 4 hetero atoms selected from a nitrogen atom, a sulfur atom and an oxygen atom and the like.

Examples of the ring formed by two of $R^4$, $R^5$ and $R^6$, together with the silicon atom bonded thereto, include a 3- to 12-membered (preferably 5- to 10-membered) ring wherein $R^4$ and $R^5$, $R^4$ and $R^6$, or $R^5$ and $R^6$ are bonded to each other to form an alkylene group.

Examples of the ring formed by two of $R^7$, $R^8$, $R^9$, $R^{10}$ and $R^{11}$, together with the carbon atom(s) bonded thereto, include (i) a 5- to 14-membered (preferably 5- to 8-membered) hydrocarbon ring optionally having double bond(s) in the ring (e.g., $C_{5-12}$ cycloalkane, $C_{5-12}$ cycloalkene, $C_{6-14}$ arene etc., preferably $C_{5-8}$ cycloalkane, $C_{5-8}$ cycloalkene, benzene etc.), (ii) a 5- to 14-membered (preferably 5- to 10-membered) monocyclic or bicyclic heterocycle optionally having double bond(s) in the ring, which contains, besides carbon atom, 1 to 4 hetero atoms selected from a nitrogen atom, a sulfur atom and an oxygen atom and the like.

Examples of the ring formed by two of $R^{13}$, $R^{14}$ and $R^{15}$, together with the silicon atom bonded thereto, include a 3- to 12-membered (preferably 5- to 10-membered) ring wherein $R^{13}$ and $R^{14}$, $R^{13}$ and $R^{15}$, or $R^{14}$ and $R^{15}$, are bonded to each other to form an alkylene group.

Examples of the fused ring formed by $R^1$ and $R^{25}$ bonded each other and $R^{25}$ and $R^{26}$ bonded each other, together with the carbon atoms bonded thereto, include (i) a 8- to 18-membered bicyclic, tricyclic or tetracyclic fused hydrocarbon ring having at least one double bond in the ring, (ii) a 8- to 18-membered bicyclic, tricyclic or tetracyclic fused heterocycle having at least one double bond in the ring, which contains, besides carbon atom, 1 to 4 hetero atoms selected from a nitrogen atom, a sulfur atom and an oxygen atom, and the like.

In the α,β-unsaturated ketone or aldehyde compound represented by the formula (15), examples of the fused ring formed by $R^1$ and $R^{25}$ bonded each other and $R^{25}$ and $R^{26}$ bonded each other, together with the carbon atoms bonded thereto, include fused rings having an α,β-unsaturated ketone represented by the following formulas:

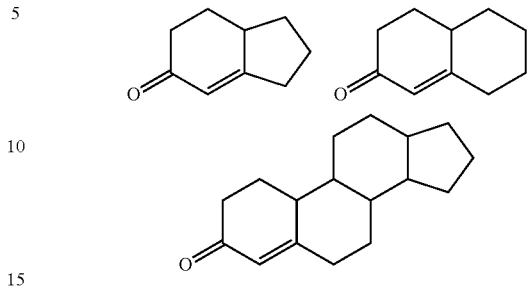

In the 1-siloxydiene compound represented by the formula (16), examples of the fused ring formed by $R^1$ and $R^{25}$ bonded each other and $R^{25}$ and $R^{26}$ bonded each other, together with the carbon atoms bonded thereto, include fused rings having a siloxydiene structure represented by the following formulas:

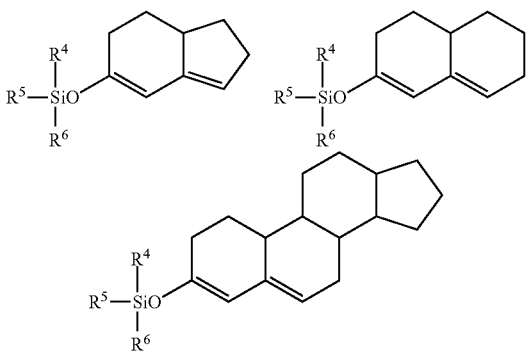

The "substituent" that these rings optionally have is not particularly limited as long as it does not influence the reaction. For example, $C_{1-8}$ alkyl group, $C_{1-8}$ alkoxy group, di($C_{1-8}$ alkyl)amino group, a halogen atom, $C_{6-14}$ aryl-$C_{1-8}$ alkyloxy group (e.g., benzyloxy, 1- or 2-naphthylmethoxy etc.), $C_{2-8}$ alkenyloxy group (e.g., allyloxy, propargyloxy etc.), nitro group, nitroso group, cyano group, $C_{1-8}$ alkylthio group, $C_{2-8}$ alkenylthio group, $C_{1-8}$ alkyl-carbonyl group (e.g., acetyl etc.), oxo group and the like can be mentioned. The number of the substituent is not particularly limited, and 1 to 3 is preferable, and the substituents may be the same or different.

When the ring has oxo groups as substituents, a product wherein two oxo groups are both silyl enol etherified can be produced by using 2 or more equivalents of an allylsilane compound.

The present invention provides a method for producing a silyl enol ether compound represented by the formula (3) (hereinafter to be referred to as silyl enol ether compound (3)), which comprises reacting a ketone or aldehyde compound represented by the formula (1) (hereinafter to be referred to as ketone or aldehyde compound (1)) with an allylsilane compound represented by the formula (2) (hereinafter to be referred to as allylsilane compound (2)), in the presence of a base and 0.00001 to 0.5 equivalents of an acid catalyst relative to ketone or aldehyde compound (1).

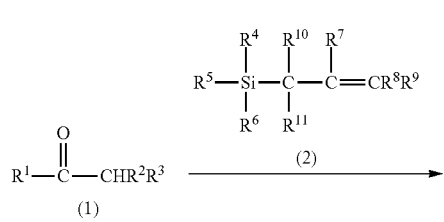

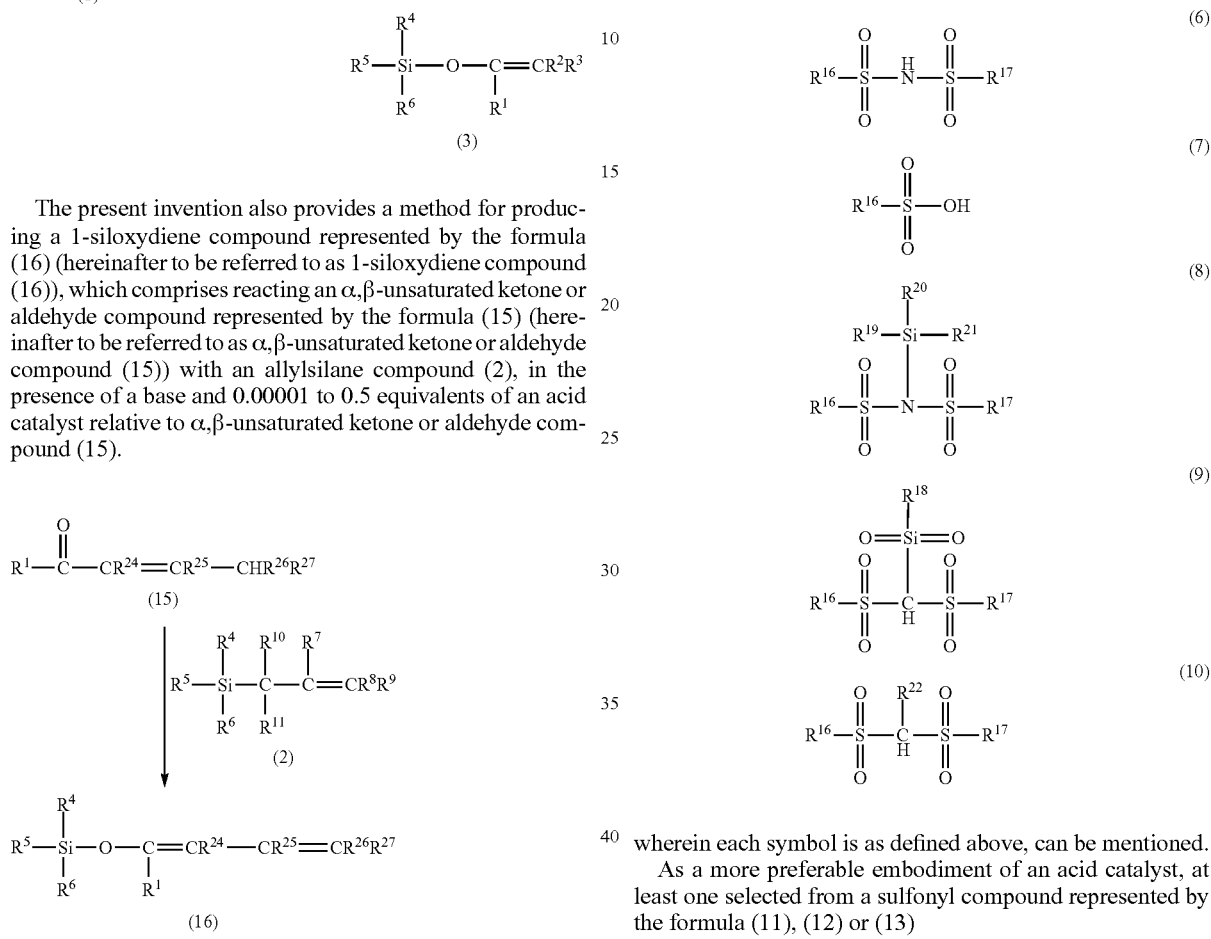

The present invention also provides a method for producing a 1-siloxydiene compound represented by the formula (16) (hereinafter to be referred to as 1-siloxydiene compound (16)), which comprises reacting an α,β-unsaturated ketone or aldehyde compound represented by the formula (15) (hereinafter to be referred to as α,β-unsaturated ketone or aldehyde compound (15)) with an allylsilane compound (2), in the presence of a base and 0.00001 to 0.5 equivalents of an acid catalyst relative to α,β-unsaturated ketone or aldehyde compound (15).

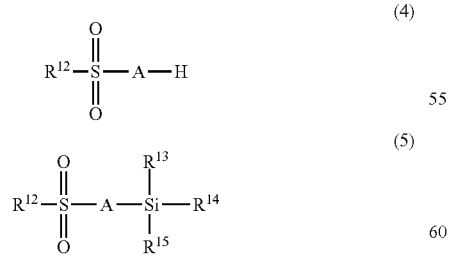

The acid catalyst to be used for the method of the present invention includes Brønsted acid catalyst and Lewis acid catalyst. For example, at least one selected from a sulfonyl compound represented by the formula (4) or (5)

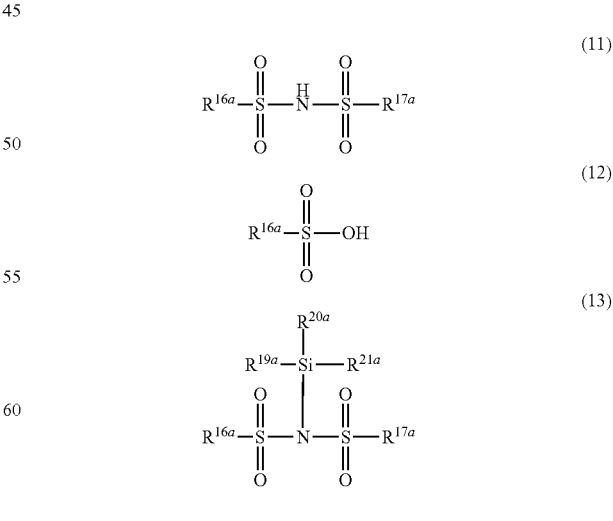

wherein each symbol is as defined above, can be used as an acid catalyst.

Preferably, an acid catalyst showing pKa of 8 or below in acetic acid can be used. For example, trifluoromethanesulfonic acid (pKa=4.2), bis(trifluoromethanesulfonyl)imide (pKa=7.8), pentafluorophenylbis(trifluoromethanesulfonyl)methane (pKa=1.5) and the like can be mentioned (pKa in acetic acid is shown in the parentheses).

As a preferable embodiment of an acid catalyst, at least one selected from a sulfonyl compound represented by the formula (6), (7), (8), (9) or (10)

wherein each symbol is as defined above, can be mentioned.

As a more preferable embodiment of an acid catalyst, at least one selected from a sulfonyl compound represented by the formula (11), (12) or (13)

wherein each symbol is as defined above, can be mentioned.

As another preferable embodiment of an acid catalyst, a sulfonyl compound represented by the formula (6)

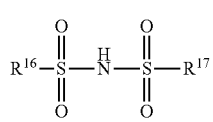

(6)

wherein each symbol is as defined above, can be mentioned.

As a particularly preferable embodiment of an acid catalyst, a sulfonyl compound represented by the formula (11)

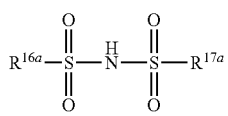

(11)

wherein each symbol is as defined above, can be mentioned.

The "nitrogen atom, oxygen atom, carbon atom, sulfur atom or phosphorus atom, which is unsubstituted or has one or more substituents as chemically allowed" includes N—R, O, C(R)$_2$, CHR, CH$_2$, S, a residue derived from phosphoric acid and the like (wherein R is a hydrogen atom or an organic group).

Examples of the "organic group" include an alkyl group optionally having substituent(s), an alkenyl group optionally having substituent(s), an alkynyl group optionally having substituent(s), a cycloalkyl group optionally having substituent(s), an aralkyl group optionally having substituent(s), an aryl group optionally having substituent(s), a heteroaryl group optionally having substituent(s), a halogen atom, a hydroxyl group, an alkoxy group, an amino group, a silyl group optionally having substituent(s) and the like.

In the formulas (6), (7), (8), (9) and (10), $R^{16}$, $R^{17}$ and $R^{18}$ are each independently an alkyl group optionally substituted by halogen atom(s), an aryl group optionally substituted by halogen atom(s) or a heterocyclic group optionally substituted by halogen atom(s), with preference given to, each independently, an alkyl group substituted by fluorine atom(s), an aryl group substituted by fluorine atom(s) or a heterocyclic group substituted by fluorine atom(s).

The "alkyl group substituted by two or more fluorine atoms" means that wherein the "alkyl group" defined above is substituted by two or more fluorine atoms. For example, trifluoromethyl, pentafluoroethyl, heptafluoropropyl, nonafluorobutyl, undecafluoropentyl, tridecafluorohexyl, pentadecafluoroheptyl, heptadecafluorooctyl and the like can be mentioned, particularly preferably trifluoromethyl.

The "aryl group substituted by two or more fluorine atoms" means that wherein the "aryl group" defined above is substituted by two or more fluorine atoms. For example, pentafluorophenyl, p-trifluoromethyltetrafluorophenyl and the like can be mentioned.

Examples of the sulfonyl compound represented by the formula (6) or (11) include bis(trifluoromethanesulfonyl)imide (to be also referred to as triflic imide), bis(nonafluorobutanesulfonyl)imide, 4,4,5,5,6,6-hexafluorodihydro-1,1,3,3-tetraoxido-4H-1,3,2-dithiazine and the like.

Examples of the sulfonyl compound represented by the formula (7) or (12) include trifluoromethanesulfonic acid, nonafluorobutanesulfonic acid, pentafluorophenylsulfonic acid and the like.

Examples of the sulfonyl compound represented by the formula (8) or (13) include bis(trifluoromethanesulfonyl)trimethylsilylimide, which is a compound represented by the formula

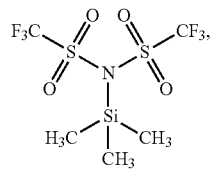

bis(trifluoromethanesulfonyl)triisopropylsilylimide, bis(trifluoromethanesulfonyl)(tert-butyldimethylsilyl)imide and the like.

Examples of the sulfonyl compound represented by the formula (9) include tris(trifluoromethanesulfonyl)methane, tris(nonafluorobutanesulfonyl)methane and the like.

Examples of the sulfonyl compound represented by the formula (10) include pentafluorophenylbis(trifluoromethanesulfonyl)methane, 1,1,3,3-tetrakis(trifluoromethanesulfonyl)propane, bis(trifluoromethanesulfonyl) methane and the like.

Of the above-mentioned acid catalysts, bis(trifluoromethanesulfonyl)imide, trifluoromethanesulfonic acid or pentafluorophenylbis(trifluoromethanesulfonyl)methane is preferably used. Particularly, bis(trifluoromethanesulfonyl) imide is preferably used as an acid catalyst.

The amount of the acid catalyst to be used is 0.00001 to 0.5 equivalents, preferably 0.001 to 0.5 equivalents, more preferably 0.001 to 0.2 equivalents, still more preferably 0.001 to 0.1 equivalents, particularly preferably 0.005 to 0.05 equivalents, relative to ketone or aldehyde compound (1) or α,β-unsaturated ketone or aldehyde compound (15).

The base to be used in the method of the present invention may be any of an organic base and an inorganic base. As the organic base, trimethylamine, triethylamine, diisopropylethylamine, pyridine, picoline, 2,6-lutidine, collidine, N-methylpyrrolidine, N-methylmorpholine, 1,8-diazabicyclo [5.4.0]undec-7-ene (DBU), 1,5-diazabicyclo[4.3.0]non-5-ene (DBN), 1,4-diazabicyclo[2.2.2]octane (DABCO) and the like can be mentioned. As the inorganic base, alkali metal carbonates such as sodium carbonate, potassium carbonate, cesium carbonate and the like; alkali metal hydrogen carbonates such as sodium hydrogen carbonate, potassium hydrogen carbonate and the like; and the like can be mentioned.

The amount of the base to be used is 0.00001 to 0.5 equivalents, preferably 0.001 to 0.5 equivalents, more preferably 0.001 to 0.2 equivalents, still more preferably 0.001 to 0.1 equivalents, particularly preferably 0.005 to 0.05 equivalents, relative to ketone or aldehyde compound (1) or α,β-unsaturated ketone or aldehyde compound (15).

By reducing the amount of the acid catalyst and the base, the amount of the reaction waste (coproduct) can be reduced. The salt of the acid catalyst and the base produced by the reaction can be recovered and reused.

In the formula (2), $R^4$, $R^5$ and $R^6$ are preferably each independently an alkyl group optionally having substituent(s), more preferably a $C_{1-8}$ alkyl group, still more preferably a $C_{1-4}$ alkyl group. In the formula (2), $R^7$ is preferably a hydrogen atom, an alkyl group, an aryl group or an aralkyl group, more preferably a hydrogen atom, a $C_{1-8}$ alkyl group, a $C_{6-14}$ aryl group or a $C_{6-14}$ aryl-$C_{1-8}$ alkyl group, still more preferably a hydrogen atom, a $C_{1-4}$ alkyl group (e.g., methyl), $C_{6-10}$ aryl group (e.g., phenyl) or phenyl-$C_{1-8}$ alkyl group. In the formula (2), $R^8$, $R^9$, $R^{10}$ and $R^{11}$ are each preferably a hydrogen atom.

Preferable examples of allylsilane compound (2) include an allyltrialkylsilane compound represented by the formula (14)

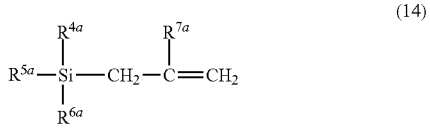

(14)

wherein $R^{4a}$, $R^{5a}$ and $R^{6a}$ are each independently an alkyl group, and $R^{7a}$ is a hydrogen atom, an alkyl group, an aryl group or an aralkyl group. In the formula (14), $R^{4a}$, $R^{5a}$ and $R^{6a}$ are preferably each independently a $C_{1-8}$ alkyl group, more preferably a $C_{1-4}$ alkyl group. In the formula (14), $R^{7a}$ is preferably a hydrogen atom, a $C_{1-8}$ alkyl group, a $C_{6-14}$ aryl group or a $C_{6-14}$ aryl-$C_{1-8}$ alkyl group, more preferably a hydrogen atom, a $C_{1-4}$ alkyl group (e.g., methyl), a $C_{6-10}$ aryl group (e.g., phenyl) or a phenyl-$C_{1-8}$ alkyl group.

Examples of the allyltrialkylsilane compound represented by the formula (14) include allyltrimethylsilane, allyltriisopropylsilane, trimethyl(2-methylallyl)silane, tert-butyldimethyl(2-methylallyl)silane, trimethyl(2-phenylallyl)silane and the like.

When allylsilane compound (2) wherein $R^7$, $R^8$, $R^9$, $R^{10}$ and $R^{11}$ are each a hydrogen atom is used as a silylating agent, the resulting wastes are gaseous propene gas ($CH_3$—$CH$=$CH_2$) and a catalytic amount of a salt of the acid catalyst and the base. When allylsilane compound (2) wherein $R^7$ is a methyl group, and $R^8$, $R^9$, $R^{10}$ and $R^{11}$ are each a hydrogen atom is used, the resulting wastes are isobutene gas (($CH_3$)$_2$C=$CH_2$) and a catalytic amount of a salt of the acid catalyst and the base. Since propene gas and isobutene gas are released from the reaction mixture, it affords an advantage that the purification method of the object silyl enol ether compound (3) or 1-siloxydiene compound (16) is convenient. The salt of the acid catalyst and the base can be recovered and reused.

When a trialkylphenylsilane compound or trialkylbenzylsilane compound is used as a silylating agent, the resulting wastes are benzene or toluene, and a catalytic amount of a salt of the acid catalyst and the base. Since benzene and toluene can be evaporated together with the reaction solvent, it affords an advantage that the purification method of the object silyl enol ether compound (3) or 1-siloxydiene compound (16) is convenient. In the same manner as above, the salt of the acid catalyst and the base can be recovered and reused.

The amount of allylsilane compound (2) to be used is 1 to 100 equivalents, preferably 1 to 5 equivalents, more preferably 1.1 to 3 equivalents, relative to ketone or aldehyde compound (1) or α,β-unsaturated ketone or aldehyde compound (15).

The reaction of the present invention is advantageously performed without solvent or in a solvent inert to the reaction. The solvent is not particularly limited as long as the reaction proceeds, and aromatic hydrocarbons such as benzene, toluene, xylene, ethylbenzene, cumene, chlorobenzene, trifluorotoluene, anisole and the like; halogenated hydrocarbons such as dichloromethane, dichloroethane, chloroform, dichlorohexane and the like; saturated hydrocarbons such as cyclopentane, methylcyclopentane, cyclohexane, methylcyclohexane, decahydronaphthalene and the like; ethers such as diethyl ether, diisopropyl ether, tetrahydrofuran, 1,4-dioxane, diethylene glycol, tert-butyl methyl ether and the like; nitriles such as acetonitrile, benzonitrile and the like; esters such as ethyl acetate, butyl acetate, propyl formate and the like; and the like can be mentioned. Preferable examples of the solvent include aromatic hydrocarbons such as benzene, toluene, xylene, ethylbenzene, cumene and the like; halogenated hydrocarbons such as dichloromethane, dichloroethane, chloroform, dichlorohexane and the like, and the like. These solvents may be used alone, or two or more solvents may be mixed at a suitable ratio as necessary, for example, 1:1 to 1:10, and used.

The amount of the solvent to be used is generally, about 0.1 to about 100 mL, preferably about 1 to about 10 mL, per 1 mmol of ketone or aldehyde compound (1) or α,β-unsaturated ketone or aldehyde compound (15).

The reaction temperature is generally about −40° C. to about 200° C., preferably about 15° C. to about 130° C. The reaction is preferably performed at room temperature (about 1° C. to about 30° C.) or under heating (near the boiling point of the solvent).

While the reaction time varies depending on the kind of ketone or aldehyde compound (1) or α,β-unsaturated ketone or aldehyde compound (15), the kind of allylsilane compound (2) to be used and reaction temperature, it is generally about 1 min to about 5 hr, preferably about 5 min to about 1 hr.

The order of addition of ketone or aldehyde compound (1) or α,β-unsaturated ketone or aldehyde compound (15), allylsilane compound (2), an acid catalyst and a base is not particularly limited. For example, a method including adding, under refluxing, allylsilane compound (2) and an acid catalyst to ketone or aldehyde compound (1) or α,β-unsaturated ketone or aldehyde compound (15) in a solvent, and adding a base to allow reaction can be mentioned.

The obtained silyl enol ether compound (3) or 1-siloxydiene compound (16) can be isolated and purified by a conventional method. For example, to the reaction mixture is added an aqueous sodium hydrogen carbonate solution, and the mixture is extracted with an organic solvent such as hexane, ethyl acetate and the like, and the organic layer is dried and concentrated under reduced pressure. The obtained product can be purified by a conventional method such as distillation, column chromatography, recrystallization and the like. Alternatively, the reaction mixture can be purified by adding an inorganic base such as solid cesium carbonate and the like (not less than the stoichiometric amount, preferably 1 to 5 equivalents, relative to the catalyst), filtering off the precipitate, evaporating the solvent of the filtrate under reduced pressure and distillation thereof.

The method of the present invention can also be performed using a microreactor as a reactor. The microreactor is not particularly limited as long as it is a microfluidic reactor used in the field of chemical synthesis. The inner diameter of the channel of the microreactor where the reaction is performed is generally within the range of 0.5 to 3000 μm, preferably 100 to 1000 μm. While the length of the channel of the microreactor where the reaction is performed is can be appropriately determined, it is generally within the range of 10 to 20000 mm, preferably 100 to 2000 mm.

As a preferable embodiment, the following method can be mentioned. A solution of the mixture of ketone or aldehyde compound (1) and allylsilane compound (2) (solution A), a solution of an acid catalyst (solution B), and a solution of a base (solution C) are prepared. Solution A and solution B are continuously supplied, and solution A and solution B are mixed in a micromixer. Solution C is continuously supplied, and mixture A-B and solution C are mixed in a micromixer. The time necessary for mixing solution A and solution B can be set to about $10^{-5}$ to $5 \times 10^3$ sec. The time necessary for mixing mixture A-B and solution C can be set to about $10^{-5}$ to $5 \times 10^3$ sec. The reaction mixture is poured into an aqueous sodium hydrogen carbonate solution, and extracted with an organic solvent such as hexane, ethyl acetate and the like. The organic layer is dried and concentrated under reduced pressure to give the object product. The obtained product can be purified by a conventional method such as distillation, column chromatography, recrystallization and the like.

A method for producing 1-siloxydiene compound (16) from α,β-unsaturated ketone or aldehyde compound (15) and allylsilane compound (2) can also be performed in the same manner as in the method explained above. That is, 1-siloxydiene compound (16) can be produced by using α,β-unsaturated ketone or aldehyde compound (15) instead of ketone or aldehyde compound (1).

As the ketone or aldehyde compound (1), α,β-unsaturated ketone or aldehyde compound (15) and allylsilane compound (2), which are starting materials, commercially available products or those produced by a known method can be used.

EXAMPLES

The present invention is more specifically explained by way of Examples, to which the present invention is not limited. In the following Examples, TMS means trimethylsilyl, TIPS means triisopropylsilyl, TBS means tert-butyldimethylsilyl, Tf means trifluoromethanesulfonyl, Ts means p-toluenesulfonyl, Me means methyl, Et means ethyl, Ph means phenyl, and $^t$Bu means tert-butyl.

Example 1

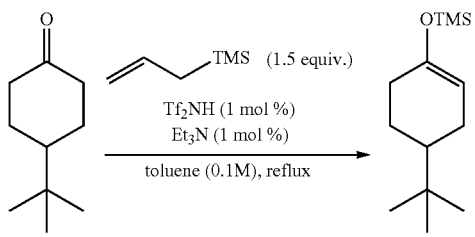

Into a two-necked flask were placed 4-tert-butylcyclohexanone (74.1 mg, 0.480 mmol), and toluene (5.0 ml) as a solvent, and the mixture was subjected to heating under reflux conditions under an argon atmosphere. After the start of the refluxing, allyltrimethylsilane (82.3 mg, 0.720 mmol) was added, and a solution (0.1 M) of triflic imide (1.35 mg, 4.80 μmol) in toluene was added dropwise. After 5 min, triethylamine (0.486 mg, 4.80 μmol) was added, and the mixture was reacted for 10 min. Thereafter, cooled aqueous sodium hydrogen carbonate solution was added, and the mixture was extracted with hexane and dried over sodium sulfate. The solvent was evaporated under reduced pressure and purified by column chromatography to give the object product 4-tert-butyl-1-trimethylsilyloxy-1-cyclohexene (yield 88%).

Example 2

Using ketones 1a, 1k, 1c, 1d and 1e described in the following Table 1 as a substrate, and in the same manner as in Example 1, the reaction was performed to give silyl enol ethers 3a, 3k, 3c and 3c', 3d and 3d', and 3e and 3e', respectively. The resultant products were purified by distillation or column chromatography. The yield and isomer ratio are shown in Table 1.

TABLE 1

| substrate | product | | yield (%) |
|---|---|---|---|
| 1a | 3a | | 82 |
| 1b | 3b | | 88 |
| 1k | 3k | | 97 |
| 1c | 3c | 3c' | 94 (87:13) |
| 1d | 3d | 3d' | 89 (93:7) |
| 1e | 3e | 3e' | 96 (98:2) |

Example 3

Using ketones 1f, 1g, 1h, 1i and 1j described in the following Table 2 as a substrate and allyltriisopropylsilane (3 equivalents relative to the substrate) instead of allyltrimethylsilane, and in the same manner as in Example 1, the reaction was performed to give silyl enol ethers 4f, 4g, 4h and 4h', 4i and 4i', and 4j, respectively. The resultant products were purified by distillation or column chromatography. The yield and isomer ratio are shown in Table 2.

TABLE 2

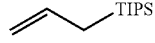

| substrate | product | yield (%) |
|---|---|---|
| 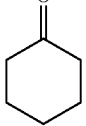<br>1f | 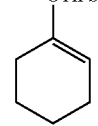<br>4f | 92 |
| 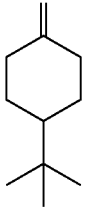<br>1g | 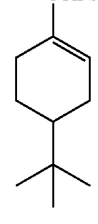<br>4g | 91 |
| 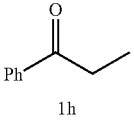<br>1h | 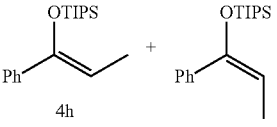<br>4h  +  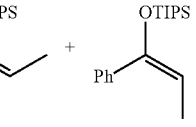<br>4h' | 72<br>(77:23) |
| 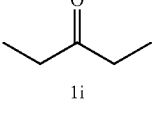<br>1i | 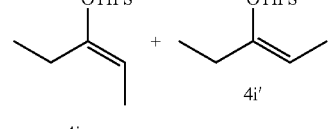<br>4i  +  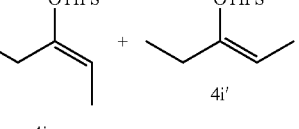<br>4i' | 70<br>(73:27) |
| 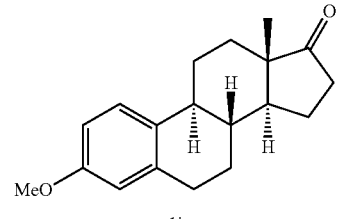<br>1j | 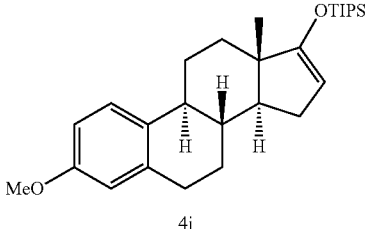<br>4j | 54 |

Example 4

Using ketones or an aldehyde described in the following Table 3-1 and Table 3-2 as a substrate and trimethyl(2-methylallyl)silane instead of allyltrimethylsilane, and in the same manner as in Example 1, the reaction was performed to give silyl enol ethers. The reaction temperature was room temperature (25° C.) The resultant products were purified by distillation or column chromatography. The yield and isomer ratio are shown in Table 3-1 and Table 3-2.

TABLE 3-1

| substrate | product | yield (%) |
|---|---|---|
| 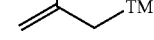 |  | 94 |
|  |  | 98 |
|  |  | 97 |
|  | 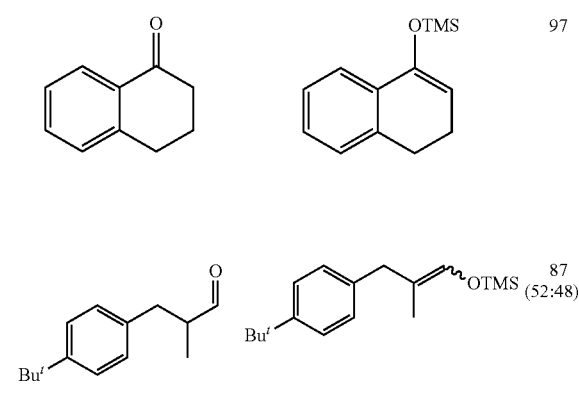 | 87 (52:48)[a] |

[a] geometric isomerism of E/Z isomers has not been determined.

TABLE 3-2

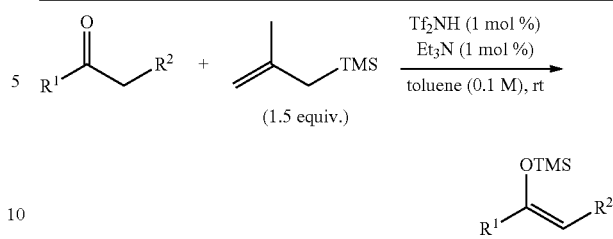

| substrate | product | yield (%) |
|---|---|---|

(cyclohexanone, 2-methyl) → OTMS + OTMS products: 95 (91:9)

(cyclopentanone, 2-methyl) → OTMS + OTMS products: 88 (93:7)

(Ph-propan-1-one) → OTMS + OTMS products: 95 (98:2)

(Ph-CH2Cl ketone) → OTMS-Cl + OTMS-Cl products: 71 (98:2)

(4-tBu-cyclohexanone) → OTMS product: 95

Example 5

Using ketones described in the following. Table 4 as a substrate and tert-butyldimethyl(2-methylallyl)silane instead of allyltrimethylsilane, and in the same manner as in Example 1, the reaction was performed to give silyl enol ethers. The reaction temperature was room temperature (25° C.). The resultant products were purified by distillation or column chromatography. The yield is shown in Table 4.

TABLE 4

TABLE 4-continued

| substrate | product | yield (%) |
|---|---|---|
| cyclohexanone | 1-OTBS-cyclohexene | 93 |
| 4-tBu-cyclohexanone | 4-tBu-1-OTBS-cyclohexene | 94 |

Example 6

Using α,β-unsaturated ketone compounds described in Table 5 as a substrate and trimethyl(2-methylallyl)silane instead of allyltrimethylsilane, and in the same manner as in Example 1, the reaction was performed to give silyl enol ethers. The reaction temperature was room temperature (25° C.). The resultant products were purified by distillation or column chromatography. The yield is shown in Table 5.

TABLE 5

| substrate | product | yield (%) |
|---|---|---|
| (bicyclic dione) | (TMSO bicyclic enone) | 68 |
| (bicyclic dione) | (bis-TMSO bicyclic dienol) | 91[a] |
| (steroid dione with Me groups) | (TMSO steroid dienol) | 86 |

[a] 2.5 equivalents of trimethyl(2-methylallyl) silane was used

Example 7

Using α,β-unsaturated ketone compounds described in Table 6 as a substrate and tert-butyldimethyl(2-methylallyl) silane instead of allyltrimethylsilane, and in the same manner as in Example 1, the reaction was performed to give silyl enol ethers. The reaction temperature was room temperature (25° C.) The resultant products were purified by distillation or column chromatography. The yield is shown in Table 6.

TABLE 6

| substrate | product | yield (%) |
|---|---|---|
| (bicyclic dione) | (TBSO bicyclic enone) | 64 |
| (bicyclic dione) | (bis-TBSO bicyclic dienol) | 94[a] |

[a] 2.5 equivalents of tert-butyldimethyl(2-methylallyl) silane was used

Example 8

Using ketone 1c described in the following Table 7 as a substrate and trimethyl(2-methylallyl)silane instead of allyl-trimethylsilane, and in the same manner as in Example 1, the reaction was performed to give silyl enol ethers 3c and 3c'. The reaction temperature was refluxing temperature (about 120° C.) (entry 1), room temperature (about 25° C.) (entry 2) and −40° C. (entry 3), and the reaction time was 10 to 30 min. The resultant products were purified by distillation or column chromatography. The yield and isomer ratio are shown in Table 7.

When trimethyl(2-methylallyl)silane was used as a silylating agent, the reaction proceeded even at −40° C.

TABLE 7

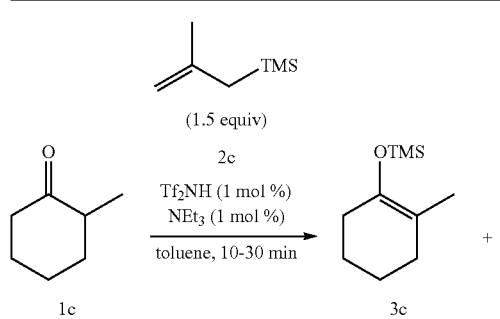

TABLE 7-continued

| | | | |
|---|---|---|---|
| 2 | room temperature (about 25° C.) | 95 | 91:9 |
| 3 | −40° C. | 46 | 97:3 |

Example 9

A microreactor can also be utilized as a reactor. In this case, the reaction time could be shortened, and the amount of the silylating agent could be reduced to 1 equivalent relative to the substrate.

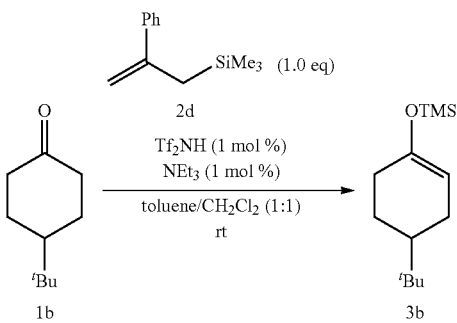

schematic diagram of microreactor system

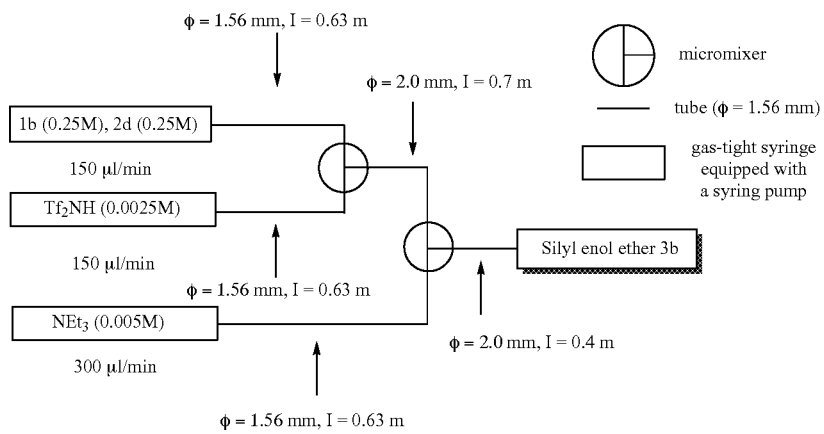

TABLE 7-continued

| entry | temperature | yield of (3c + 3c') (%) | isomer ratio 3c:3c' |
|---|---|---|---|
| 1 | reflux (about 120° C.) | 98 | 92:8 |

A solution (2.0 ml) of the mixture of 4-tert-butylcyclohexanone (1b) (77.1 mg, 0.500 mmol, 0.250 M) and trimethyl(2-phenylallyl)silane (2d) (85.2 mg, 0.500 mmol, 0.250 M) in toluene/dichloromethane (1:1, volume ratio), solution (2.0 ml) of Tf$_2$NH (1.41 mg, 5.00 μmol, 2.50 mM) in toluene/dichloromethane (1:1, volume ratio), and a solution (5.0 ml) of NEt$_3$ (2.53 mg, 25.0 μmol, 5.00 mM) in toluene/dichloromethane (1:1, volume ratio) were used as solution A, solution B and solution C, respectively. The three kinds of solutions were each loaded in a gas tight syringe, and set on a syringe pump as shown in the above-mentioned schematic diagram. Using a microreactor (manufactured by Techno Applications Co., Ltd., COMET-X01) at room temperature, solution A and solution B were continuously supplied at a flow rate of 150 μl/min, and solution C was supplied at a flow rate of 300 μl/min. A micromixer was set at a place where solution A and solution B were mixed, and a micromixer was also set at a place where mixture A-B and solution C were mixed. A flask containing ice-cooled aqueous sodium hydrogen carbonate solution was set at the outlet of the reaction mixture, and the mixture of A, B and C was collected there. After completion of the reaction, the recovered product was extracted with hexane and the organic layer was dried over sodium sulfate. After filtration, the solvent was evaporated under reduced pressure to give the object product, 4-tert-butyl-1-trimethylsilyloxy-1-cyclohexene (3b) (yield 90%). The time necessary for mixing solution A and solution B (calculated from distance between the two micromixers and flow rate) was 145 sec, and the time necessary for mixing mixture A-B and solution C (calculated from distance from the second micromixer to reaction mixture outlet and flow rate) was 40 sec.

The $^1$H NMR spectrum data of the compounds obtained in the above-mentioned Examples are shown in the following.

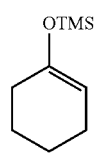

3a 1-trimethylsilyloxycyclohexene $^1$H NMR (400 MHz, CDCl$_3$): δ 0.18 (s, 9H), 1.48-1.50 (m, 2H), 1.63-1.69 (m, 2H), 1.97-2.03 (m, 4H), 4.86-4.88 (m, 1H).

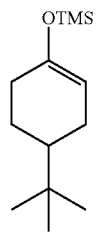

3b 4-tert-butyl-1-trimethylsilyloxy-1-cyclohexene $^1$H NMR (400 MHz, CDCl$_3$): δ 0.19 (s, 9H), 0.90 (s, 9H), 1.21-1.29 (m, 2H), 1.78-1.85 (m, 2H), 1.98-2.09 (m, 3H), 4.84-4.86 (m, 1H).

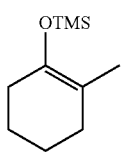

3c 1-trimethylsilyloxy-2-methyl-1-cyclohexene (major isomer)

$^1$H NMR (500 MHz, CDCl$_3$): δ 0.12 (s, 9H), 1.43 (s, 3H), 1.51-1.80 (m, 2H), 1.91-2.04 (m, 6H).

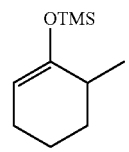

3c'

1-trimethylsilyloxy-6-methyl-1-cyclohexane (minor isomer)

$^1$H NMR (500 MHz, CDCl$_3$): δ 0.18 (s, 9H), 1.02 (d, 3H, J=7.0 Hz), 1.20-1.81 (m, 5H), 2.01 (m, 2H), 4.75 (td, 1H, J=3.9, 1.2 Hz).

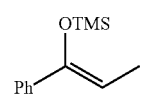

3d (Z)-1-phenyl-1-(trimethylsilyloxy)-1-propene (major isomer)

$^1$H NMR (500 MHz, CDCl$_3$): δ 0.13 (s, 9H), 1.73 (d, 3H, J=7.3 Hz), 5.11 (q, 1H, J=7.3 Hz), 7.23-7.31 (m, 3H), 7.45-7.46 (m, 2H).

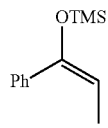

3d'

(E)-1-phenyl-1-(trimethylsilyloxy)-1-propene (minor isomer)

$^1$H NMR (500 MHz, CDCl$_3$): δ 0.13 (s, 9H), 1.76 (d, 3H, J=7.3 Hz), 5.33 (q, 1H, J=7.3 Hz), 7.23-7.31 (m, 3H), 7.45-7.46 (m, 2H).

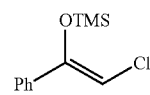

3e (Z)-2-chloro-1-phenyl-1-(trimethylsilyloxy)ethylene (major isomer)

$^1$H NMR (500 MHz, CDCl$_3$): δ 0.22 (s, 9H), 5.95 (s, 1H), 7.31-7.35 (m, 3H), 7.43-7.46 (m, 2H).

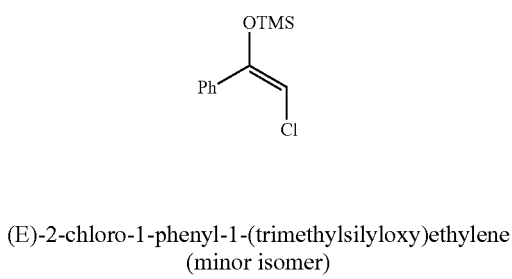

3e′

(E)-2-chloro-1-phenyl-1-(trimethylsilyloxy)ethylene (minor isomer)

$^1$HNMR (500 MHz, CDCl$_3$): δ 0.15 (s, 9H), 5.79 (s, 1H), 7.29-7.30 (m, 3H), 7.64-7.66 (m, 2H).

4f 1-triisopropylsilyloxycyclohexene $^1$H NMR (500 MHz, CDCl$_3$): δ 1.07-1.14 (m, 21H), 1.50 (m, 2H), 1.65 (m, 2H), 1.99 (m, 2H), 2.04 (m, 2H), 4.87 (m, 1H).

4g 4-tert-butyl-1-(triisopropylsilyloxy)cyclohexene $^1$H NMR (500 MHz, CDCl$_3$): δ 0.90 (s, 9H), 1.11-1.17 (m, 21H), 1.84 (m, 2H), 2.06 (m, 2H), 2.11 (m, 1H), 4.88 (m, 1H).

4h (Z)-1-phenyl-1-(triisopropylsilyloxy)-1-propene (major isomer)

$^1$H NMR (500 MHz, CDCl$_3$): δ 1.04-1.06 (m, 21H), 1.77 (d, 3H, J=6.9 Hz), 5.05 (q, 4H, J=6.9 Hz), 7.26-7.28 (m, 3H), 7.43-7.45 (m, 2H).

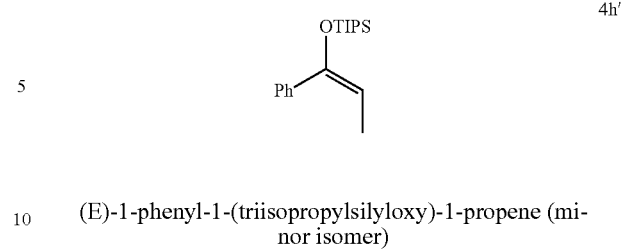

4h′

(E)-1-phenyl-1-(triisopropylsilyloxy)-1-propene (minor isomer)

$^1$H NMR (500 MHz, CDCl$_3$): δ 1.04-1.06 (m, 21H), 1.69 (d, 3H, J=7.2 Hz), 5.09 (q, 1H, J=7.2 Hz), 7.21-7.24 (m, 3H), 7.32-7.35 (m, 2H).

4i (E)-3-(triisopropylsilyloxy)-2-pentene (major isomer)

$^1$H NMR (500 MHz, CDCl$_3$): δ 1.05-1.11 (m, 24H), 1.56 (dt, 3H, J=6.6, 1.2 Hz), 2.07 (m, 2H), 4.41 (qt, 1H, J=6.6, 1.2 Hz).

4i′

(Z)-3-(triisopropylsilyloxy)-2-pentene (minor isomer)

$^1$HNMR (500 MHz, CDCl$_3$): δ 1.05-1.11 (m, 24H), 1.58 (dt, 3H, J=8.0, 1.2 Hz), 2.09-2.13 (m, 2H), 4.55 (q, 1H, J=6.8 Hz).

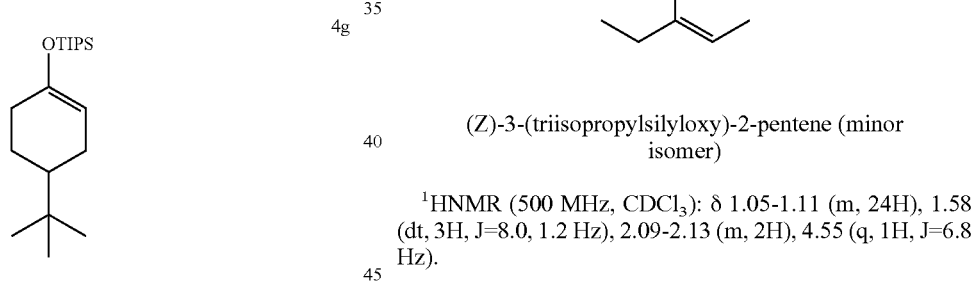

4h $^1$H NMR (500 MHz, CDCl$_3$): δ 0.89 (s, 3H), 1.01-1.09 (m, 21H), 1.53 (m, 6H), 1.98-1.93 (m, 1H), 2.09-2.20 (m, 1H), 2.26 (dt, 1H, J=10.4 Hz), 2.43-2.36 (m, 1H), 2.50 (dd, 1H, J=19.6, 7.9 Hz), 2.87-2.93 (m, 2H), 3.77 (s, 3H), 4.42-4.43 (m, 1H), 6.65 (d, 1H, J=2.3 Hz), 6.72 (dd, 1H, J=9.0, 2.3 Hz), 7.21 (d, 1H, J=8.6 Hz).

INDUSTRIAL APPLICABILITY

The silyl enol ethers produced by the method of the present invention are reactive intermediates important for the organic synthesis, and utilized as synthetic intermediates for pharmaceutical products and organic materials, or treatment agents in various fields of surface treatment.

For example, for the synthesis of carbapenem antibiotics (thienamycin, biapenem and the like), silyl enol ether is used for the production of 4-siloxy-β-lactam compound, which is the most fundamental synthetic intermediate. In addition, silyl enol ether is used for the synthesis of thienamycins, using 4-acetoxy-β-lactam compound as a starting material (JP-A-6-199780).

Moreover, in organic chemistry, silyl enol ethers are equivalent compounds of metal enolate represented by the formula

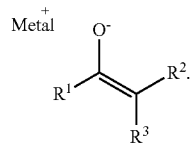

Due to very high reactivity, it is difficult to use metal enolate itself by isolation and purification. As compared to them, silyl enol ether is more stable, can be isolated and purified, and easy to use as an organic synthesis starting material. The silyl enol ethers produced by the method of the present invention can be used as an equivalent compound of metal enolate instead of metal enolate in the production of pharmaceutical products and the like utilizing metal enolate.

This application is based on patent application No. 2010-48290 filed in Japan, which is incorporated by reference herein in its entirety.

The invention claimed is:

1. A method for producing a silyl enol ether compound represented by the formula (3)

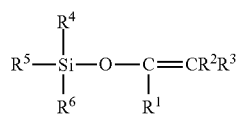

wherein $R^1$ is an alkyl group optionally having substituent(s), a cycloalkyl group optionally having substituent(s), an aralkyl group optionally having substituent(s), an alkenyl group optionally having substituent(s), an alkynyl group optionally having substituent(s), an aryl group optionally having substituent(s) or a heteroaryl group optionally having substituent(s);

$R^2$ and $R^3$ are each independently a hydrogen atom, a halogen atom, an alkyl group optionally having substituent(s), a cycloalkyl group optionally having substituent(s), an aralkyl group optionally having substituent(s), an aryl group optionally having substituent(s) or a heteroaryl group optionally having substituent(s);

$R^1$ and $R^3$, $R^1$ and $R^2$, or $R^2$ and $R^3$ optionally form, together with the carbon atom(s) bonded thereto, a ring optionally having substituent(s);

$R^4$, $R^5$ and $R^6$ are each independently a hydrogen atom, a halogen atom, an alkoxy group optionally having substituent(s), an aryloxy group optionally having substituent(s), an alkyl group optionally having substituent(s), an alkenyl group optionally having substituent(s), an alkynyl group optionally having substituent(s), a cycloalkyl group optionally having substituent(s), a cycloalkenyl group optionally having substituent(s), an aralkyl group optionally having substituent(s), an aryl group optionally having substituent(s), a heteroaryl group optionally having substituent(s) or a silyl group optionally having substituent(s); and two of $R^4$, $R^5$ and $R^6$ optionally form a ring together with the silicon atom bonded thereto, which comprises reacting a ketone compound represented by the formula (1)

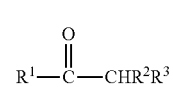

wherein each symbol is as defined above, with an allylsilane compound represented by the formula (2)

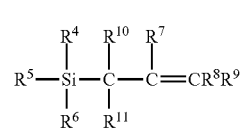

wherein $R^7$, $R^8$, $R^9$, $R^{10}$ and $R^{11}$ are each independently a hydrogen atom, an alkyl group optionally having substituent(s), an alkenyl group optionally having substituent(s), an alkynyl group optionally having substituent(s), a cycloalkyl group optionally having substituent(s), a cycloalkenyl group optionally having substituent(s), an aralkyl group optionally having substituent(s), an aryl group optionally having substituent(s), a heteroaryl group optionally having substituent(s), a halogen atom, a hydroxyl group, an alkoxy group, an amino group or a silyl group optionally having substituent(s);

two of $R^7$, $R^8$, $R^9$, $R^{10}$ and $R^{11}$ optionally form, together with the carbon atom(s) bonded thereto, a ring optionally having substituent(s); and other symbols are as defined above, in the presence of one mol % each tertiary amine base and triflic imide relative to a ketone compound represented by the formula (1).

2. A method for producing a 1-siloxydiene compound represented by the formula (16)

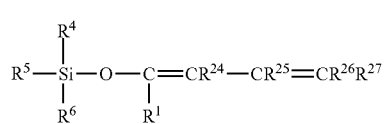

wherein $R^1$ is an alkyl group optionally having substituent(s), a cycloalkyl group optionally having substituent(s), an aralkyl group optionally having substituent(s), an alkenyl group optionally having substituent(s), an alkynyl group optionally having substituent(s), an aryl group optionally having substituent(s) or a heteroaryl group optionally having substituent(s);

$R^4$, $R^5$ and $R^6$ are each independently a hydrogen atom, a halogen atom, an alkoxy group optionally having substituent(s), an aryloxy group optionally having substituent(s), an alkyl group optionally having substituent(s), an alkenyl group optionally having substituent(s), an alkynyl group optionally having substituent(s), a cycloalkyl group optionally having substituent(s), a cycloalkenyl group optionally having substituent(s), an aralkyl group optionally having substituent(s), an aryl group optionally having substituent(s), a heteroaryl group optionally having substituent(s) or a silyl group optionally having substituent(s);

two of $R^4$, $R^5$ and $R^6$ optionally form a ring together with the silicon atom bonded thereto;

$R^{24}$, $R^{25}$ and $R^{26}$ and $R^{27}$ are each independently a hydrogen atom, a halogen atom, an alkyl group optionally having substituent(s), a cycloalkyl group optionally having substituent(s), an aralkyl group optionally having substituent(s), an aryl group optionally having substituent(s) or a heteroaryl group optionally having substituent(s); and $R^1$ and $R^{25}$, $R^{25}$ and $R^{26}$, $R^{25}$ and $R^{27}$, or $R^{26}$ and $R^{27}$ optionally form, together with the carbon atom(s) bonded thereto, a ring optionally having substituent(s); or $R^1$ and $R^{25}$ are optionally bonded, and $R^{25}$ and $R^{26}$ are optionally bonded, to form, together with the carbon atoms bonded thereto, a fused ring optionally having substituent(s), which comprises reacting an α,β-unsaturated ketone compound represented by the formula (15)

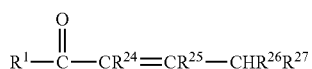
(15)

wherein each symbol is as defined above, with an allylsilane compound represented by the formula (2)

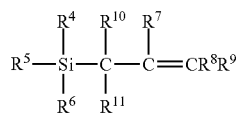
(2)

wherein $R^7$, $R^8$, $R^9$, $R^{10}$ and $R^{11}$ are each independently a hydrogen atom, an alkyl group optionally having substituent(s), an alkenyl group optionally having substituent(s), an alkynyl group optionally having substituent(s), a cycloalkyl group optionally having substituent(s), a cycloalkenyl group optionally having substituent(s), an aralkyl group optionally having substituent(s), an aryl group optionally having substituent(s), a heteroaryl group optionally having substituent(s), a halogen atom, a hydroxyl group, an alkoxy group, an amino group or a silyl group optionally having substituent(s);

two of $R^7$, $R^8$, $R^9$, $R^{10}$ and $R^{11}$ optionally form, together with the carbon atom(s) bonded thereto, a ring optionally having substituent(s); and other symbols are as defined above, in the presence of one mol % each tertiary amine base and triflic imide relative to the α,β-unsaturated ketone compound represented by the formula (15).

3. The method according to claim 1, wherein the allylsilane compound represented by the formula (2) is a compound represented by the formula (14)

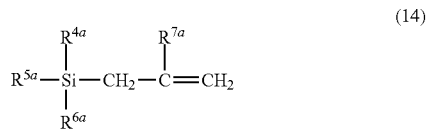
(14)

wherein $R^{4a}$, $R^{5a}$ and $R^{6a}$ are each independently an alkyl group, and $R^{7a}$ is a hydrogen atom, an alkyl group, an aryl group or an aralkyl group.

4. The method according to claim 1, wherein the reaction is performed using a microreactor.

5. The method according to claim 2, wherein the allylsilane compound represented by the formula (2) is a compound represented by the formula (14)

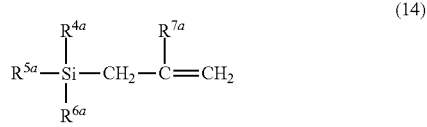
(14)

wherein $R^{4a}$, $R^{5a}$ and $R^{6a}$ are each independently an alkyl group, and $R^{7a}$ is a hydrogen atom, an alkyl group, an aryl group or an aralkyl group.

6. The method according to claim 2, wherein the reaction is performed using a microreactor.

* * * * *